United States Patent [19]

Tominaga et al.

[11] Patent Number: 5,407,677

[45] Date of Patent: Apr. 18, 1995

[54] INVIGORATING HERBAL GEL FOR SUPPLE SKIN

[75] Inventors: Naoki Tominaga, Yokohama; Toshio Yoshioka, Zushi, both of Japan

[73] Assignee: Shiseido Co., Ltd., Tokyo, Japan

[21] Appl. No.: 22,476

[22] Filed: Feb. 25, 1993

[30] Foreign Application Priority Data

Mar. 19, 1992 [JP] Japan .................................. 4-093772

[51] Int. Cl.$^6$ .............................................. A61K 7/00
[52] U.S. Cl. ................................. 424/401; 424/195.1; 514/937; 514/938
[58] Field of Search ........................... 424/401, 195.1; 514/937, 938

[56] References Cited

U.S. PATENT DOCUMENTS

| | | | |
|---|---|---|---|
| 4,525,344 | 6/1985 | Tutsky | 424/195.1 |
| 4,563,354 | 1/1986 | Chang et al. | 424/195.1 |
| 4,885,157 | 12/1989 | Fiaschetti | 424/195.1 |
| 5,153,174 | 10/1992 | Band et al. | 424/401 |
| 5,171,737 | 12/1992 | Weiner et al. | 514/938 |
| 5,211,956 | 5/1993 | Sawai et al. | 424/451 |
| 5,215,759 | 6/1993 | Mausner | 424/195.1 |
| 5,268,176 | 12/1993 | Znaiden et al. | 424/401 |

FOREIGN PATENT DOCUMENTS

| | | |
|---|---|---|
| 0217413 | 10/1986 | European Pat. Off. |
| 2231364 | 5/1974 | France |
| 60-104005 | 6/1985 | Japan |
| 61-027910 | 2/1986 | Japan |
| 8100514 | 3/1981 | WIPO |
| 9112792 | 9/1991 | WIPO |

OTHER PUBLICATIONS

Patent Abstracts of Japan; vol. 11, No. 246, Aug. 11, 1987; "External Skin Preparation"; JP-A-62-053-912.

*Primary Examiner*—Gollamudi S. Kishore
*Assistant Examiner*—Amy Hulina
*Attorney, Agent, or Firm*—Townsend & Banta

[57] ABSTRACT

An herbal composition for the body is provided which promotes lipid metabolism by increasing the activity of a lipid metabolism enzyme in the body, and which has a weight reducing effect. The composition contains at least one component selected from fennel extract, inositol and dextrane sulfate.

This composition is preferably employed in the form of an invigorating herbal gel for supple skin which is effective in increasing lipase activity and thus accelerating lipid metabolism.

2 Claims, No Drawings

INVIGORATING HERBAL GEL FOR SUPPLE SKIN

BACKGROUND OF THE INVENTION

This application claims the priority of Japanese Patent Application No. 4-93772 filed on Mar. 19, 1992, which is incorporated herein by reference.

1. Field of the Invention

This invention relates in general, to an endermic liniment for the body which characteristically contains a fennel extract, and, more specifically, to an invigorating herbal gel for supple skin which is effective in increasing lipase activity and thus accelerating lipid metabolism.

2. Description of Related Art

In order to reduce excess fat in the body and thus maintain a well-defined body, various exercises and restrictive diets have been used and cosmetics gels and creams have also been used for body massage to accelerate internal metabolism. Thus far, however, no endermic liniment has been discovered with weight reducing effects which targets lipase, an enzyme which aids in lipid metabolism.

It is therefore an object of the invention to provide a substance which increases lipase activity in the body and thus accelerate lipid metabolism.

SUMMARY OF THE INVENTION

An invigorating herbal composition for the body contains one or more components chosen from among fennel extracts, inositol and dextran sulfate. The fennel extract can be obtained using water or a hydrophilic organic solvent such as alcohol, or mixtures thereof. In a preferred embodiment, the fennel extracts can be used alone with excellent results. In another preferred embodiment, the fennel extract is used in combination with inositol and dextran sulfate. This composition increases the activity of lipase which increases lipid metabolism and promotes weight reduction.

DESCRIPTION OF THE PREFERRED EMBODIMENTS

The fennel extract used in the present invention can be obtained, by a number of procedures. For example, adding water to thinly sliced fennel and extraction at 50° C. for a prescribed duration, filtering the extract, and then concentrating it as desired. Alternatively, 30 vol % ethanol can be added to thinly sliced fennel and extraction carried out at 60° C. for a prescribed duration, filtering the extract, and then concentrating it as desired. Also, 60 vol % ethanol can be added to fennel powder and extraction carried out at 100° C. for a prescribed duration, filtering the extract, and then concentrating it as desired.

The content of fennel extract is preferably 0.001-30 wt %, more preferably 0.01-5 wt %, of the total endermic liniment. By fennel extract is meant the fennel extract on a dry basis without the solvent used in the extraction process.

There is no particular limitation regarding the manufacturing process of the inositol used in the present invention. The content of the inositol is preferably 0.001-30 wt %, more preferably 0.01-5 wt %, of the total endermic liniment.

For the dextran sulfate used in this invention, either sodium dextran sulfate or potassium dextran sulfate can be used, but sodium dextran sulfate is more preferable. The content of the dextran sulfate is preferably 0.001-30 wt %, more preferably 0.01-5 wt %, of the total endermic liniment.

For the endermic liniment of this invention, one or more components chosen from the above described fennel extract, inositol and dextran sulfate can be used individually or in combination. Of these, the fennel extract is particularly preferable. Also, compared with individual use, a combination of two or more of these components produces an endermic liniment for the body with even higher lipase activity and lipid metabolism acceleration.

The endermic liniment for the body of the present invention may contain, as necessary, in the range which does not affect the efficacy of this invention, the following various components which are generally used in cosmetics and medicines: vitamin A's such as vitamin oil, retinol and retinol acetate, vitamin B2's such as riboflavin, riboflavin lactate and flavin adenine dinucleotide, vitamin B6's such as pyridoxine hydrochloride and pyridoxine dioctenoate, vitamin C's such as L-ascorbic acid, L-ascorbyl dipalmitate, sodium-L-ascorbyl-2-sulfate, L-ascorbyl-2- phosphate and dipotassium-DL-α-tocopherol-L-ascorbyl phosphate, pantothenic acids such as calcium pantothenate, D-pantothenyl alcohol, pantothenyl ethylether and acetyl pantothenyl ethylether, vitamin D's such as ergocalciferol and cholecalciferol, nicotinic acids such as nicotinic acid, nicotinic-acid amide and benzyl niacinate, vitamin E's such as alpha-tocopherol, tocopherol acetate, DL-alpha-tocopherol niacinate and DL-alpha-tocopherol succinate, vitamins such as vitamin P and biotin, oils such as avocado oil, palm oil, peanut oil, beef tallow, rice bran oil, jojoba oil, evening primrose oil, carnauba wax, lanolin, liquid paraffin, squalane, isostearyl palmitate, isostearyl alcohol and tri-2-glyceryl ethylhexanoate, one or more humectants such as glycerine, sorbitol, polyethylene glycol, 1,3-butylene glycol, collagen, hyaluronic acid and chondroitin sulfate, ultra violet light absorbents such as paradimethyl amino amyl benzoate, methoxy octyl cinnamate, 4-tert-butyl-4-methoxydibenzoilmethane, diparamethoxy cinnamic glyceryl mono-2-ethylhexanoate, 2-hydroxy-4-methoxybenzophenon, 2-hydroxy-4-methoxybenzophenon-5-sodium sulfonate, urocanic acid and diisopropyl ethyl cinnamate, antioxidants such as sodium erythorbate and parahydroxy anisole, surfactants such as sodium stearyl sulfate, diethanolamine cetyl sulfate, cetyltrimethyl ammonium saccharin, polyethylene glycol isostearate, glyceryl arachidate, diglycerine diisostearate and phospholipid, preservatives such as ethylparabene and butylparabene, antiphlogistics such as glycyrrhizic acid derivatives, glycyrrhetinic acid derivatives, salicylic acid derivatives, hinokitiol, zinc oxide and allantoin, skin whitening agents such as placenta extract, glutathione and creeping saxifrage extract, extracts from Amur cork, gold thread, purple root, peony, Japanese green gentian, birch, sage, loquat, carrot, aloe, mallow, iris, grape, adlay seeds, dishcloth gourd, lily, saffron, cnidium rhizome, ginger, Saint-John's wort, prickly restharrow, rosemary and garlic, royal jelly, activators such as phosensitive elements, cholesterol derivatives and calf blood extracts, blood circulation accelerators such as gamma-oryzanol, anti-seborrhea agents such as sulfur and thiantol, thickners such as carboxyvinyl polymers, carboxymethyl cellulose and carboxyhydroxy propyl cellulose, perfumes, water, alcohol, coloring materials such as titanium yellow, carthamin and safflower, and resin powder such as polyethylene and nylon. The endermic liniment of this invention can take any form. It can take the form of oil, solubilized lotions, emulsified systems such as milky lotions and creams, or ointments, dispersed liquid powder products and such.

The effects of the present invention are described herein by reference to experimental data. as set forth in the following examples.

EXAMPLE 1

The lipase activity acceleration effect of the fennel extract, inositol and dextran sulfate.

Triolein is added to a polyvinyl alcohol solution and the solution is emulsified by a homogenizer. Lipase, which has a lipid decomposition action, is added to this triolein solution, and the reaction is carried out at 37° C. for a fixed amount of time. At that time, the fennel extract, inositol or dextran sulfate is added separately or in combinations.

The fatty acid released from decomposed triolein is titrated with a sodium hydroxide solution.

The results of the experiment are shown below.
(1) Water extract of fennel
   Sample Titration volume (ml)
   Control 3.8±0.4
   Fennel extract 6.1±0.7
(2) 30% alcohol extract of fennel
   Sample Titration volume (ml)
   Control 1.3±0.2
   Fennel extract 3.7±0.5
(3) 613% alcohol extract of fennel
   Sample Titration volume (ml)
   Control 0.4±0.1
   Fennel extract 3.0±0.2
(4) Inositol
   Sample Titration volume (ml)
   Control 3.5±0.4
   Inositol 4.0±0.3
(5) Dextran sulfate
   Sample Titration volume (ml)
   Control 3.6±0.4
   Sodium dextran sulfate 5.1±0.3
(6) 60% alcohol extract of fennel and dextran sulfate
   Sample Titration volume (ml)
   Control 2.2±0.3
   Fennel extract+Sodium dextran sulfate 10.5±0.2
(7) 30% alcohol extract of fennel and inositol
   Sample Titration volume (ml)
   Control 3.1±0.3
   Fennel extract+Inositol 11.3±0.3
(8) Fennel extract, inositol and dextran sulfate
   Sample Titration volume (ml)
   Control 3.5±0.3
   Fennel extract+Dextran sulfate+Inositol 14.3±0.3 mean±SD A greater titration volume indicates accelerated lipid decomposition, releasing more fatty acid.

The results shown above indicate that the fennel extract, inositol and dextran sulfate are effective in accelerating the lipase activity, and that the combined use of the fennel extract, inositol and dextran sulfate shows a particularly high degree of lipase activity acceleration. For the fennel extract, the activation effect of accelerating multiplication of skin cells (fibroblasts) was also observed.

EXAMPLE 2

Lipid metabolism effect.

For the sample with the highest lipid decomposition action, the lipid metabolim effect was evaluated using the following method.

Ninety women in their twenties and thirties were instructed to apply the milky lotion of Example 5 all over their bodies every morning and night continuously for 3 months. After this continuous application, the body fat ratio (ratio of total fat in a body) was measured by an instrument which uses near infrared light reflection (body fat meter BFT-2000, manufactured by Ketto Kagaku Co. Ltd.). Forty of the 90 women were chosen as the control group for whom the fennel extract, inositol and dextran sulfate were absent in the milky lotion. The averages of the body fat ratio measurements were calculated.

The results are shown in Table 1.

TABLE 1

|  | Before Continuous Application | After Continuous Application |
| --- | --- | --- |
| Control | 34.7 ± 5.6 | 32.0 ± 6.0 |
| Fennel extract + Dextran sulfate + Inositol | 36.2 ± 4.8 | 28.3 ± 6.3 |

Twelve women in their twenties and thirties were instructed to apply the milky lotion of Example 5 all over their bodies every morning and night continuously for 3 months. After this continuous application, the body fat ratio (ratio of total fat in a body) was measured by an instrument which uses near infrared light reflection (body fat meter BFT-2000, manufactured by Ketto Kagaku Co. Ltd.). Six of the 12 women were chosen as the control group for whom the fennel extract, inositol and dextran sulfate were absent in the milky lotion. The averages of the body fat ratio measurements were calculated.

The results are shown in Table 2.

TABLE 2

|  | Panel | Before Application | After 3 Month Continuous Application |
| --- | --- | --- | --- |
| Control |  |  |  |
|  | A | 30.0 | 31.5 |
|  | B | 29.5 | 26.0 |
|  | C | 35.0 | 32.0 |
|  | D | 37.0 | 37.5 |
|  | E | 39.0 | 37.5 |
|  | F | 35.5 | 33.0 |
| Average |  | 34.33 | 32.92 |
| Fennel extract, Dextran sulfate Inositol |  |  |  |
|  | G | 39.8 | 29.0 |
|  | H | 30.0 | 26.5 |
|  | I | 32.0 | 25.5 |
|  | J | 36.8 | 30.5 |
|  | K | 40.5 | 29.5 |
|  | L | 35.0 | 28.0 |
| Average |  | 35.68 | 28.17 |

As clearly shown in the results shown above, this invention shows a remarkable reduction in the body fat ratio compared with the control group.

This invention is described in detail by referring to examples. This invention is not limited to these examples. The contents are in wt % units.

EXAMPLE 3

A lotion is prepared as follows:

(1) Fennel extract 0.5
(2) Tocopherol acetate 0.01
(3) Glycerine 4.0
(4) 1,3-butylene glycol 4.0
(5) Inositol 0.1
(6) Ethanol 7.0
(7) Polyoxyethylene (60) oleyl alcohol ether 0.5
(8) Methyl parabene 0.2
(9) Citric acid 0.05
(10) Sodium citrate 0.1
(11) Perfume 0.05
(12) Purified water Balance Citric acid, sodium citrate, glycerine, 1,3-butylene glycol, inositol and the fennel extract are dissolved in purified water (water phase). Separately, polyoxyethylene oleyl alcohol ether, tocopherol acetate, perfume and methyl parabene are dissolved in ethanol, and this is added to said water phase, solubilized and filtered to obtain a lotion.

EXAMPLE 4

A cream is prepared according to the following procedure.
(1) Cetostearyl alcohol 3.5
(2) Squalene 40.0
(3) Bees wax 3.0
(4) Reduced lanolin 5.0
(5) Ethyl parabene 0.3
(6) Polyoxyethylene (20) sorbitanmonopalmitinic ester 2.0
(7) Monoglyceride stearate 2.0
(8) Sodium N-stearoilglutamate 0.5
(9) 2-hydroxy-4-methoxybenzophenon 1.0
(10) Retinol acetate 2.0
(11) Evening primrose oil 0.05
(12) Perfume 0.03
(13) Fennel extract 1.0
(14) 1,3-butyleneglycol 5.0
(15) Potassium dextran sulfate 0.1
(16) Purified water Balance Items (1) through (12) are heat-melted/dissolved and added, while stirring, to a mixture of items (13) through (16), which have been heated to 75° C. After making the emulsified particles finer by using a homogenizing mixer, it is rapidly cooled by stirring to obtain the cream.

EXAMPLE 5

A milky lotion is prepared as follows:
(1) Steraric acid 1.5
(2) Cetyl alcohol 0.5
(3) Bees wax 2.0
(4) Polyoxyethylene (10) monooleic ester 1.0
(5) Methoxy octyl cinnamate 2.0
(6) Birch extract 0.2
(7) Fennel extract 5.0
(8) Sodium hyaluronate 0.01
(9) Triethanol amine 0.75
(10) Glycerine 7.0
(11) Inositol 5.0
(12) Sodium dextran sulfate 5.0
(13) Ethyl parabene 0.3
(14) Perfume 0.03
(15) Purified water Balance The birch extract, the fennel extract, sodium hyaluronate, glycerine, inositol, sodium dextran sulfate and triethanol amine are added to the purified water and the temperature is maintained at 70° C. (water phase). Other components are mixed and heat-melted/dissolved, and the temperature is maintained at 70° C. (oil phase). The oil phase is added to the water phase, the preliminary emulsification is conducted, and then the mixture is homogeneously emulsified using a homogenizing mixer. The milky lotion is then obtained after a rapid cooling while stirring.

EXAMPLE 6

A foam-mask is prepared as follows:
(1) Fennel extract 0.1
(2) Inositol 0.1
(3) 1,3-butylene glycol 5.0
(4) Glycerine 7.0
(5) Methyl parabene 0.1
(6) Potassium hydroxide 0.15
(7) Stearic acid 0.5
(8) Myristic acid 1.0
(9) Batyl alcohol 1.5
(10) Polyoxyethylene (60) hardened castor oil 3.0
(11) Perfume 0.05
(12) Liquefied petroleum gas 6.0
(13) Dimethyl ether 3.0
(14) Purified water Balance Items (1) through (6) are added to item (14) and heat-melted/dissolved at 70° C., items (7) through (11), stirred and heated to 75° C., are added to this mixture, and the resultant mixture is thoroughly stirred and then cooled. A container is filled with this mixture, and lastly with items (12) and (13), as a spraying agent, to obtain a foam-mask.

EXAMPLE 7

An ointment is prepared as follows:
(1) Fennel extract 10.0
(2) Tocopherol acetate 1.0
(3) Retinol palmitate 0.5
(4) Stearyl alcohol 18.0
(5) Japan tallow 20.0
(6) Polyoxyethylene (20) monooleic ester 0.25
(7) Glycerine monostearic ester 0.3
(8) Vaseline 40.0
(9) Purified water Balance The fennel extract is added to the purified water and the temperature is maintained at 70° C. (water phase). The rest of the components are mixed and melted at 70° C. (oil phase). The oil phase is added to the water phase, the mixture is homogeneously emulsified using a homogenizing mixer and then cooled to obtain an ointment.

EXAMPLE 8

A milky lotion for massage is prepared as follows:
(1) Stearic acid 1.5
(2) Cetyl alcohol 0.5
(3) Polyoxyethylene (10) monooleic ester 1.0
(4) Vaseline 3.0
(5) Squalane 10.0
(6) Liquid paraffin 5.0
(7) Glycerine 7.0
(8) 1,3-butylene glycol 5.0
(9) Triethanol amine 0.75
(10) Tocopherol acetate 0.05
(11) Fennel extract 1.0
(12) Ethyl parabene 0.25
(13) Perfume 0.02
(14) Purified water Balance The fennel extract, glycerine, 1,3-butylene glycol and triethanol amine are added to the purified water and the temperature is maintained at 70° C. (water phase). The other components are mixed and heat-melted/dissolved, and the temperature is maintained at 70° C. (oil phase). The oil phase is added to the water phase, the preliminary emulsification is conducted, and then the mixture is homogeneously emulsified using a homogenizing mixer. A milky lotion for massage is then obtained after a rapid cooling while stirring.

EXAMPLE 9

A gel for massage is prepared as follows:
(1) Sodium dextran sulfate 2.0
(2) 1,3-butyleneglycol 5.0
(3) Ethanol 10.0
(4) Carboxy vinyl polymer 0.25
(5) Polyoxyethylene oleil alcohol ether 0.5
(6) Tocopherol acetate 0.01
(7) Methyl parabene 0.15
(8) Potassium hydroxide 0.08
(9) Perfume 0.15
(10) Purified water Balance Sodium dextran sulfate, 1,3-butyleneglycol and carboxy vinyl polymer are dissolved in purified water. Then, polyoxyethylene oleil alcohol ether, tocopherol acetate, methyl parabene and perfume dissolved in ethanol are added to it. Potassium hydroxide is added to the mixture to obtain the gel for massage.

EXAMPLE 10

A cosmetic liquid is prepared as follows:
(1) Inositol 1.5
(2) Potassium dextran sulfate 1.5
(3) Fennel extract 10.0
(4) Placenta extract 0.5
(5) Sodium hyaluronate 0.01
(6) Glycerine 10.0
(7) 1,3-butyleneglycol 5.0
(8) Carboxy vinyl polymer 0.3
(9) Ethanol 7.0
(10) Polyoxyethylene (60) oleil alcohol ether 0.8
(11) Macademia nut oil 0.1
(12) Evening primrose oil 0.01
(13) Tocopherol acetate 0.01
(14) Methyl parabene 0.15
(15) Perfume Appropriate amount
(16) Potassium hydroxide 0.08
(17) Purified water Balance Items (1) through (8) are dissolved in item (17). Items (10) through (15) dissolved in item (9) are added to it. Then, item (16) is added to obtain the cosmetic liquid.

The endermic liniment of the present invention, characteristically containing one or more components chosen among a fennel extract, inositol and dextran sulfate, increases the lipase activity and shows the superior effect of accelerating lipid metabolism.

What is claimed is:

1. An invigorating herbal composition for supple skin comprising fennel extract, inositol and dextran sulfate in a carrier.

2. An invigorating herbal composition for supple skin comprising fennel extract, inositol and dextran sulfate in a carrier selected from the group consisting of an oil, lotion, cream, foam mask, ointment, gel, and milky lotion.

* * * * *